US012653422B2

(12) United States Patent
Chavey

(10) Patent No.: US 12,653,422 B2
(45) **Date of Patent: *Jun. 16, 2026**

(54) METHOD AND DEVICE FOR DIAGNOSING ANTERIOR CRUCIATE LIGAMENT INJURY SUSCEPTIBILITY

(71) Applicant: Lindsey Chavey, Overland Park, KS (US)

(72) Inventor: Lindsey Chavey, Overland Park, KS (US)

(73) Assignee: Lindsey Chavey, Overland Park, KS (US)

( * ) Notice: Subject to any disclaimer, the term of this patent is extended or adjusted under 35 U.S.C. 154(b) by 533 days.

This patent is subject to a terminal disclaimer.

(21) Appl. No.: 18/076,185

(22) Filed: Dec. 6, 2022

(65) Prior Publication Data

US 2023/0096206 A1     Mar. 30, 2023

Related U.S. Application Data

(62) Division of application No. 16/373,010, filed on Apr. 2, 2019, now Pat. No. 11,517,220.

(Continued)

(51) Int. Cl.
*A61B 5/11*          (2006.01)
*A61B 5/00*          (2006.01)
(Continued)

(52) U.S. Cl.
CPC ........... *A61B 5/1121* (2013.01); *A61B 5/1114* (2013.01); *A61B 5/4528* (2013.01);
(Continued)

(58) Field of Classification Search
CPC ....... A61B 5/11; A61B 5/1114; A61B 5/1121; A61B 5/1122; A61B 5/1126;
(Continued)

(56) References Cited

U.S. PATENT DOCUMENTS

| | | | |
|---|---|---|---|
| 11,698,384 B2 * | 7/2023 | Crockford | C12N 1/06 600/595 |
| 2009/0024062 A1 * | 1/2009 | Einarsson | A61F 5/01 600/595 |

(Continued)

OTHER PUBLICATIONS

Kim, K., J., et al., "Measurement of lower limb segmental excursion using inertial sensors during single limb stance", Journal of Biomechanics, vol. 71, pp. 151-158 (2018).

(Continued)

*Primary Examiner* — Adam J Eiseman
(74) *Attorney, Agent, or Firm* — SHOOK, HARDY & BACON L.L.P.

(57) ABSTRACT

Systems, devices, and methods are disclosed for the purpose of quantitatively determining the susceptibility of a human subject to injure their Anterior Cruciate Ligament (ACL). A method for determining injury susceptibility scores or risk categories includes determining hip extension angles and knee varus angles during the performance of a stork test and determining hip abduction angles during a squat test. Determination of angles during certain movements may be achieved using various systems and devices, including wearable devices.

18 Claims, 5 Drawing Sheets

Related U.S. Application Data

(60) Provisional application No. 62/652,410, filed on Apr. 4, 2018.

(51) Int. Cl.
  *A61B 5/103* (2006.01)
  *A61B 5/107* (2006.01)

(52) U.S. Cl.
  CPC .......... *A61B 5/4571* (2013.01); *A61B 5/4585* (2013.01); *A61B 5/6804* (2013.01); *A61B 5/1038* (2013.01); *A61B 5/1075* (2013.01); *A61B 5/1126* (2013.01); *A61B 5/7225* (2013.01)

(58) Field of Classification Search
  CPC ... A61B 5/4528; A61B 5/4533; A61B 5/4571; A61B 5/4585
  See application file for complete search history.

(56) References Cited

U.S. PATENT DOCUMENTS

| | | | | |
|---|---|---|---|---|
| 2015/0328032 | A1* | 11/2015 | Walker | A61F 5/0109 602/26 |
| 2016/0242646 | A1* | 8/2016 | Obma | A61B 5/01 |
| 2017/0042467 | A1* | 2/2017 | Herr | A61B 5/112 |
| 2017/0213437 | A1* | 7/2017 | Sundaram | G08B 21/0453 |
| 2017/0238849 | A1* | 8/2017 | Chapman | A61B 5/4576 |
| 2018/0008196 | A1* | 1/2018 | Connor | A61B 5/1126 |
| 2018/0015284 | A1* | 1/2018 | Coleman | G16H 40/63 |
| 2018/0020954 | A1 | 1/2018 | Lillie et al. | |
| 2018/0028109 | A1* | 2/2018 | Tesnow | A61B 5/742 |
| 2018/0140225 | A1* | 5/2018 | Gong | A61B 5/1071 |
| 2018/0289324 | A1* | 10/2018 | Kianifar | A61B 5/1121 |
| 2019/0117156 | A1* | 4/2019 | Howard | A61B 5/746 |
| 2019/0172585 | A1 | 6/2019 | Mazumder et al. | |
| 2021/0236025 | A1* | 8/2021 | Comtois | A61B 5/6804 |
| 2021/0393427 | A1* | 12/2021 | Mirza | A61F 5/0109 |

OTHER PUBLICATIONS

Tainaka, K., et al., "Limited hip rotation and non-contact anterior cruciate ligament injury: A case-control study", The Knee, vol. 21, pp. 86-90 (2014).

Yasuda, T., et al., "Hip rotation as a risk factor of anterior cruciate ligament injury in female athletes", The Journal of Physical Fitness and Sports Medicine, vol. 5, No. 1, pp. 105-113 (2016).

Bates, N., A., and Hewett, T., E., "Motion Analysis and the Anterior Cruciate Ligament: Classification of Injury Risk", J Knee Surg., vol. 29, No. 2, pp. 1-18 (2016).

Alentorn-Geli, E., et al., "Prevention of non-contact anterior cruciate ligament injuries in soccer players. Part 2: A review of prevention programs aimed to modify risk factors and to reduce injury rates", Knee Surg Sports Traumatol Arthrosc, vol. 17, pp. 859-879 (2009).

* cited by examiner

400

410
DETERMINE HIP EXTENSION
ANGLE DURING STORK TEST

420
DETERMINE KNEE VARUS
ANGLE DURING STORK TEST

430
DETERMINE HIP ABDUCTION
ANGLE DURING SQUAT TEST

440
DETERMINE SUSCEPTIBILITY
SCORE

450
DETERMINE RISK CATEGORY

METHOD AND DEVICE FOR DIAGNOSING ANTERIOR CRUCIATE LIGAMENT INJURY SUSCEPTIBILITY

CROSS-REFERENCE TO RELATED APPLICATIONS AND PRIORITY CLAIM

This application, entitled "Device for Diagnosing Anterior Cruciate Ligament Injury Susceptibility," is a divisional of co-pending U.S. patent application Ser. No. 16/373,010, filed on Apr. 2, 2019, which claims the benefit of U.S. Provisional Patent Application No. 62/652,410, filed Apr. 4, 2018, and entitled "Method and Device for Diagnosing Anterior Cruciate Ligament Injury Susceptibility," the entireties of which are incorporated here by reference.

BACKGROUND

The Anterior Cruciate Ligament (ACL) is a ligament within the knee that connects the femur to the tibia. One of the most common knee injuries is a sprain or tear of the ACL. Injury to the ACL is more prevalent in athletes than non-athletes, and particularly more likely for athletes participating in activities that require sudden changes in speed or direction of movement, or a twisting force, such as soccer, basketball, and football. Recovery from an ACL injury depends on the severity of the injury. In some instances, an ACL strain is treated through rest, ice, stretching, and physical therapy. Partial or complete tears of the ACL are often treated through invasive, expensive, and time-consuming surgery. Whether a strain or a tear, recovery from an ACL injury can take several weeks or months, and repeat injury is not uncommon. Thus, preventing ACL injuries is much more effective than treating an injury.

Conventionally, susceptibility of ACL injuries is determined through qualitative means. Certified athletic trainers and physical therapists may put an athlete through a battery of motions or conduct a physical exam to subjectively determine if an ACL is irritated, which may indicate likelihood of future ACL injury. Such subjectivity and qualitative diagnostic methods are imprecise, error-prone, and vary with the experience of the diagnostician. Athletes and their medical staff lack a method for quantitatively and objectively identifying a particular athlete's susceptibility for ACL injury—regardless of what particular maneuvers the athlete is likely to perform.

SUMMARY

A method is provided for quantitatively determining a person's susceptibility of injuring an ACL. Using body mechanics tests such as the stork test and the squat test, certain angles associated with ranges of movements are determined. Those angles are processed through a susceptibility score algorithm to determine a person's physiologic susceptibility of injuring an ACL. Effectively and objectively identifying athletes, in particular, who are physiologically more susceptible to injuring an ACL can permit physical therapists, certified athletic trainers, doctors, coaches, and the like, to take proactive steps to guard against ACL injury. Such proactive steps may include physical therapy, stretching, and/or strength training to increase or decrease ranges of movement. Alternatively, braces or other therapeutic or motion-restrictive devices may be used to reduce a wearer's ability to manipulate portions of the body in a way that may be more likely to cause injury (e.g., twisting of the knee).

Embodiments of the present disclosure are directed to systems and devices for obtaining measurement data and/or determining the susceptibility score. Wearable devices, such as a garment or a brace can determine ranges or motion using a plurality of sensors. Those sensors, whether analog or digital, may provide information to a processor that permits calculation of the range of movement of certain portions of the body. Those determinations may comprise the same angles needed for use in the ACL susceptibility score algorithm. Using wearable devices to obtain the measurement data and/or the susceptibility score itself creates an easy and user-operable way to prevent injury to the ACL, potentially avoiding an expensive and time-consuming recovery.

Some embodiments of this disclosure may be utilized more broadly as a method to identify variables and weights for use in susceptibility score calculation of non-ACL injuries. Using a particular order of motion-based testing and regressive processing, it is possible to identify physiologic variables most likely associated with injury susceptibility. In aspects, this information could be used to train-away from or prevent injuries to various portions of the body, including without limitation, the MCL and hip flexors, or to prevent or mitigate the effects of physiologic conditions such as shin splints or plantar fasciitis.

BRIEF DESCRIPTION OF THE DRAWINGS

Embodiments are described in detail below with reference to the attached drawing figures, wherein.

DETAILED DESCRIPTION

Figure 1:
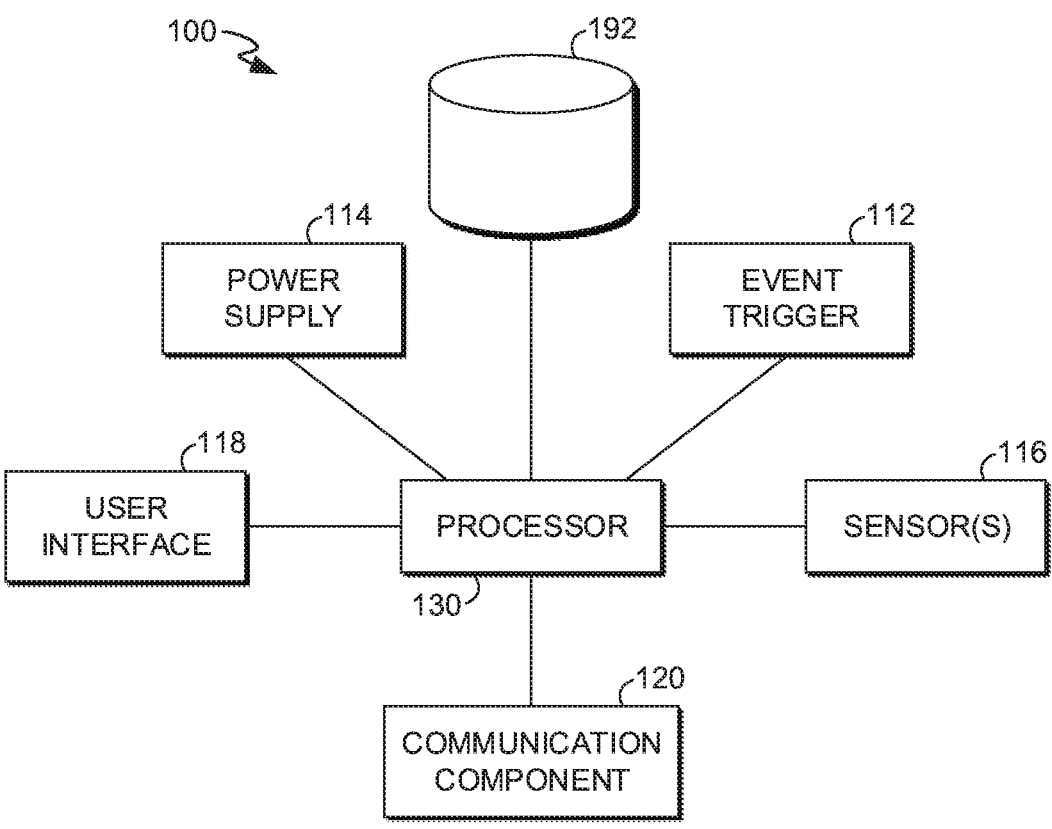
FIG. 1 depicts a block diagram of an aspect of a system in accordance with embodiments of this disclosure.

The subject matter of this disclosure is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the present disclosure may be embodied as, among other things: a method, system, or set of instructions embodied on one or more computer readable media. Accordingly, the embodiments may take the form of a hardware embodiment, a software embodiment, or an embodiment combining software and hardware. Embodiments may comprise a computer-program product that includes computer-usable instructions embodied on one or more computer readable media.

Computer-readable media include both volatile and non-volatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or storage devices. These technologies can store data momentarily, temporarily, or permanently.

By way of the present disclosure, a method is provided for identifying a human subject's physiologic susceptibility of injuring an ACL. The human subject is subjected to a stork test to determine a first value characterizing a range of motion associated with hip extension. The same or a second stork test is used to determine a second value characterizing an angle associated with knee varus. The human subject is also subjected to a squat test to determine a third value characterizing a range of motion associated with hip abduction. A susceptibility score is then calculated, positively weighing the first value and the third value and negatively weighing the second value. Human subjects having a higher susceptibility score are at a higher risk for developing an ACL injury. Said another way, subjects having a higher susceptibility score are more physiologically prone to injuring an ACL.

Systems and devices for determining the values associated with the susceptibility score are also provided. Systems and devices, such as wearable devices, may be used to determine or monitor ACL injury susceptibility by determining or monitoring bodily movements of the wearer. Wearable devices may comprise a housing for retaining the one or more sensors and processors necessary to perform the determining and monitoring functions, while holding the sensors in approximately a constant location with respect to aspects of the wearer's body. Disposed on or within the housing, a first plurality of sensors is configured to measure a range of motion associated with hip extension, particularly during a stork test. A second plurality of sensors is configured to measure an angle associated with knee varus, particularly during a stork test. A third plurality of sensors is configured to measure a range of motion associated with hip abduction, particularly during the completion of a squat. The wearable device also comprises at least one processor for obtaining measurement data from the pluralities of sensors, processing the measurement data into angular data and/or a susceptibility score, and storing and/or communicating the angular data, susceptibility score, and/or risk category to a user interface.

Turning now to FIG. 1, an aspect of a system for implementing an embodiment of this disclosure is provided. FIG. 1 depicts a block diagram of an illustrative system designated generally as reference numeral 100. Certain items are shown in block-diagram form for being able to reference something consistent with the nature of a patent, not necessarily to imply that a certain component is or is not part of a certain device, apparatus, garment, or the like. Similarly, although some items are depicted in the singular form, plural items are contemplated as well (e.g., what is shown as one data store might really be multiple data stores distributed across multiple locations). But showing every variation of each item might obscure the embodiments of this disclosure. Thus for readability, reference items are shown in the singular (while fully contemplating, where applicable, the plural).

As shown in FIG. 1, system 100 includes one or more sensors 116. In one embodiment, sensors 116 comprise one or more transducers or other sensors operable for providing electrical signals corresponding to measurements of various conditions, states, or movements of a user. In embodiments, sensors 116 may comprise a piezoresistor, accelerometers, 3-axis motion sensor, flex sensor, or other device, chiefly relying on piezoresistive or piezoelectric effect, to measure movements or locations in space. In aspects, the sensors 116 may be powered by a power supply 114. In embodiments, the power supply 114 comprises a battery for wireless operation. In other embodiments, the power supply comprises a wired electrical connection to an AC or DC power input.

In some embodiments, sensor 116 comprises a motion sensor such as a digital accelerometer or 3-axis motion sensor, a stride sensor, such as the telemetry Polar 53+ED stride sensor, manufactured by Polar Electro Inc. of Lake Success, NY, which in some embodiments may be used with in conjunction with a Polar RS800CX® sports watch with a personal-area network (PAN). In an embodiment, sensor 116 comprises a USB 3-axis 16-bit 8 GB flash memory accelerometer ("X16-Mini®", Gulf Coast Data Concepts LLC, Waveland, MS 39576).

In some embodiments, sensor 116, processor 130, communications component 120, and user interface 118 are collocated in a single device which may be worn by the user, while in other embodiments, sensor 116, processing component 130, communications component 120, and user interface 118 may be embodied in separate devices. For example, in one embodiment, sensor 116 is worn on a user's knee while processor 130, communication component 120, and user interface 118 are worn on the wrist like a watch. In another embodiment, processor 130 and user interface 118 are embodied on the user's smart phone or mobile device and communicate with sensor 116 via the communication component, both of which may be worn in the same location by the user. In yet other embodiments, the sensors 116, processor 130, communication component 120, power supply 114, and storage 192 are located in proximity to one another as components of a wearable device communicatively coupled to an external user interface 118 via communication component 120. In some embodiments, sensor 116 may communicate with processor 130 via the communication component 120 using a wireless communication protocol, such as those of existing so called "personal area network" technologies employed by exercise and fitness equipment manufacturers, for example Polar Electro, Nike, and others.

In some embodiments, multiple sensors 116 may be employed on or about the user. One or more sensors may become compromised, and having multiple sensors provides for redundancy. For example, a sensor on the lateral portion of the knee may be damaged in an athletic move, such as a soccer slide, while a second sensor on the medial portion of the knee may remain operational. In embodiments, multiple sensors at different locations on the user's body may be employed to obtain more accurate or thorough kinetic information. In such embodiments, motion-signals corresponding to motion in a particular direction or motion may be averaged, or may be weighted or scaled according to the location of the sensor. For example, an angle between a right anterior knee sensor and a left anterior hip sensor may be averaged with an angle between a right posterior knee sensor and a left posterior hip sensor.

In embodiments, communication component 120 transfers data from the sensors 116 and/or processor 130 to the user interface 118 and/or the storage 192. In aspects, the communication component 120 may communicate raw data in the form of electrical voltages, resistance, current, etc., from the sensors 116 to the processor 130. In other aspects, the communication component 120 may communicate angular data in the form of angles associated with particular bodily movements to a user interface 118. In aspects, the user interface 118 may be an electronic device wherein the size of the display limits the ability to display the full breadth of the angular data. In such an aspect, the processor 130 may process the angular data to generate a susceptibility score and/or risk category that summarizes the angular data, and cause the summarized data to be displayed on the user interface 118. It is envisioned that if a user specifically desired to view or interact with the full data set, that the processor 130 may cause the entire data set to be displayed on the user interface 118.

In aspects, the communication component 120 may comprise an input/output port, providing a means for a detachably wired connection with the processor 130, storage 192, and/or user interface 118. The input/output port may be configured for various-sized wired connections, including USB, USB 2.0, micro-USB, lightning connector, or USB-C. In other aspects, the communication component may communicate raw data to the processor 130, storage 192, and/or user interface 118 via a hard-wired connection or a plug-in wired connection not designed to be manipulated by a user, such as detachable multi-pin connector. In some aspects, communication component 120 may communicate wirelessly with the processor 130, storage 192, and/or the user interface 118 using any one or more of a variety of wireless data protocols such as near field communication (NFC), Bluetooth, 802.11 (Wi-Fi), or the like.

The processor 130 may include one or more computer storage medium, that when executed via the processor 130, cause the processor to translate raw data received from the sensors 116 into angular data. The raw data may be raw positional data, voltage, changes in voltage, resistance, and the like. In aspects, the processor comprises an event clock or timer for correlating raw data from the sensors 116. For example, at time T+1, the processor may translate raw positional data from a right knee varus sensor into a first angular entry at T+1 and translate raw positional data from a left knee varus sensor into a second angular entry at T+1. In aspects, the processor 130 may average a left sensor and a right sensor to create a single mean entry per sensor pair. For example at time T+2, the processor may translate raw positional data from a left hip abduction sensor and a right hip abduction sensor into a single mean hip abduction angle entry correlating with time T+2. As used herein, angular data or angular entries are used to mean an angle realized at the one or more sensors 116, which may be in degrees or radians, and may be relative to a reference point or absolute.

In some embodiments, system 100 further comprises an event trigger 112. The event trigger 112 highlights a particular motion, action, or event. In aspects, the event trigger 112 may comprise a button, switch, or other touch-activated or pressure-sensitive device for manual operation. In other aspects, the event trigger may be automatically triggered based on a preset condition, such as an angle from any one or more sensors 116 exceeding a threshold. Activation of the event trigger 112, whether manual or automatic, may result in the processor 130 creating a flag in the data set or adding a value, changing a binary value, or the like, to indicate that the data warrants particular attention. In aspects, the processor 130 and event trigger 112 work in combination to temporally limit the highlighted data. Such a temporal limit may be 5, 10, 30, or 60 seconds, for example.

Figures 2A, 2B:
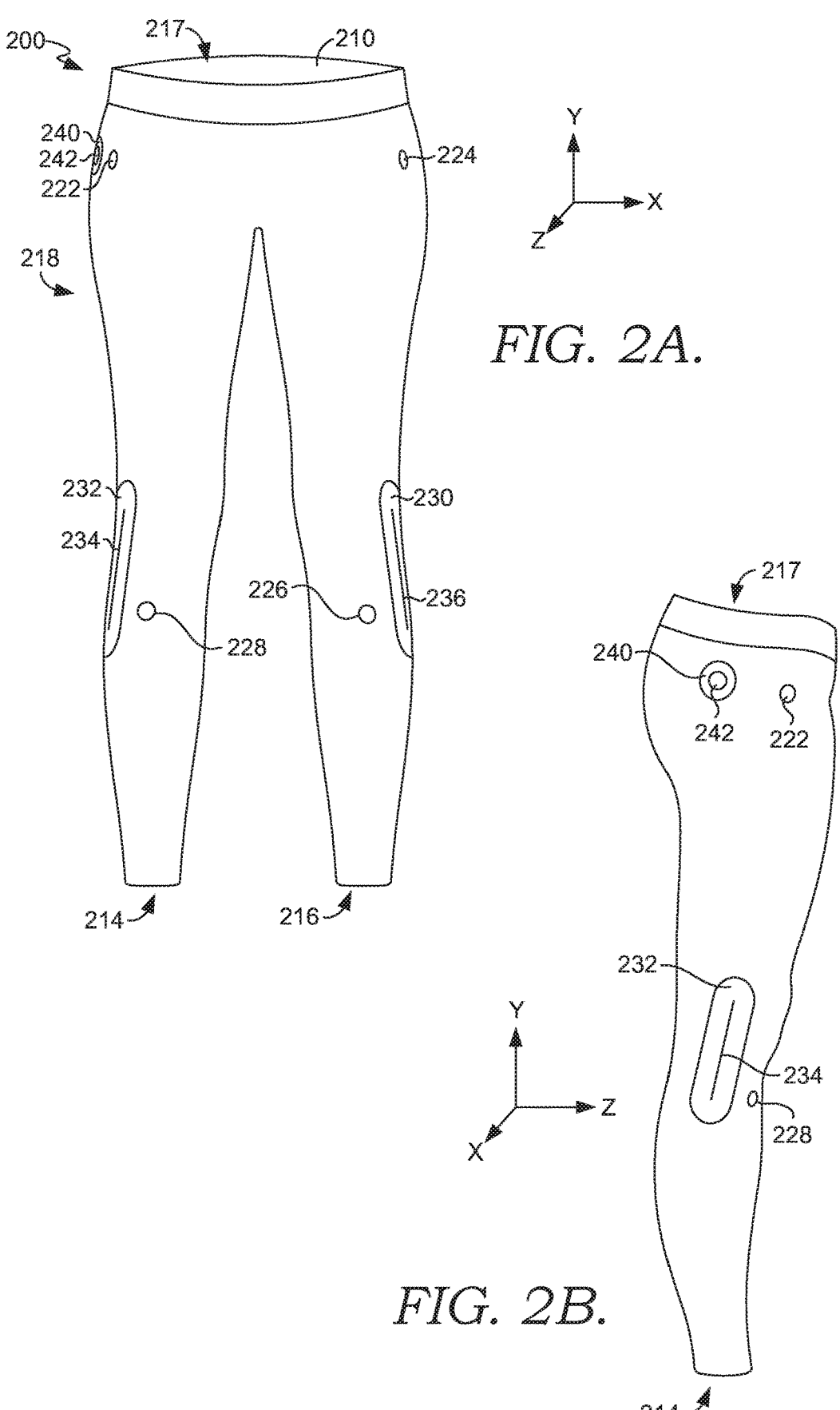
FIGS. 2A-2C depict aspects of illustrative wearable devices suitable for practicing an embodiment of this disclosure.
Figure 2C:
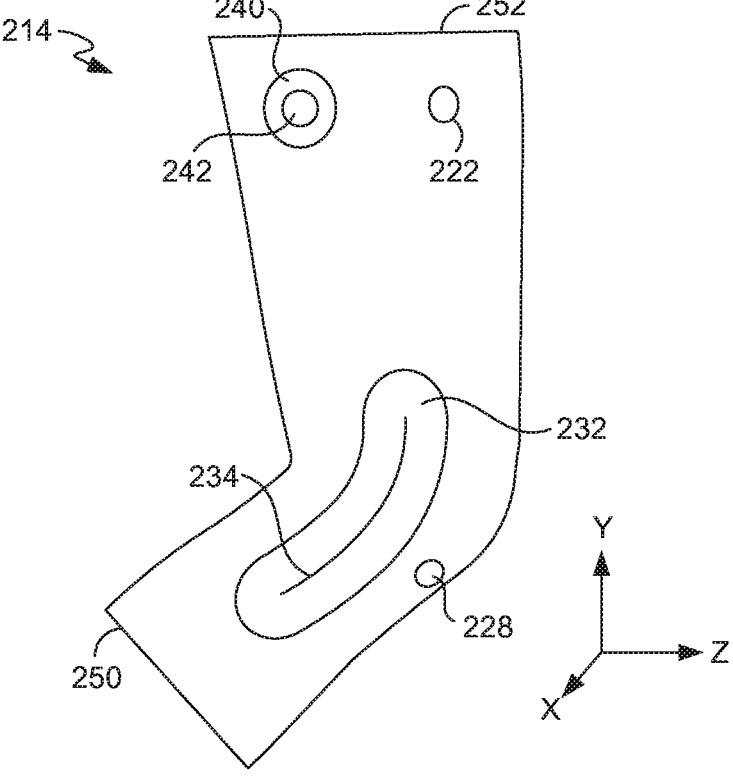

Turning now to FIGS. 2A-2C, aspects in accordance with the present disclosure are depicted. Wearable devices are disclosed for the purpose of determining angular measurements of certain portions of a human subject's body during certain movements. Wearable devices may comprise various housings, such as a garment or a brace. FIGS. 2A and 2B depict a wearable device 200 comprising a housing, such as pants, trousers, leggings, tights, compression pants, or the like, configured to contain a plurality of components (FIG. 2B is a side view of the wearable device 200 of FIG. 2A). FIG. 2C depicts an alternate embodiment of a wearable device 214 comprising a housing in the form of a brace, wrap, band, or the like. In all embodiments, it is envisioned that wearable devices of the present disclosure may be configured such that the measurement and/or processing components may be detached from the housing garment (in order to wash the housing, for example) or configured/embedded into the housing such that they are not readily removable.

Returning now to FIGS. 2A and 2B, a wearable device 200 may comprise a garment 218, a plurality of sensors (e.g., a right knee varus extension sensor 234), an event trigger 242, and a processor 240. The garment 218 may be of any type that is suitable for wear by a human subject while retaining the measurement and processing components in the as-designed configuration. In aspects, the garment 218 may comprise two layers of a textile, with the measurement and processing components disposed therebetween. In other aspects, the garment 218 may comprise a textile with padding, a backing layer, or other suitable material that may be coupled to at least one surface of the garment 218 and configured to house and protect measurement and processing components. In aspects, the garment 218 may comprise an opening for a wearer's torso at the proximal end 217, a right leg opening 214, and a left leg opening 216 at the distal end. In aspects, the garment may comprise a retention means 210 for keeping the proximal end 217 in place on wearer's body when in an as-worn configuration, such as a belt, drawstring, compression portion, waist band, Velcro, etc.

Wearable device 200 may further comprise a plurality of sensors. In aspects, the wearable device 200 may comprise a means for measuring or determining right knee flexion or extension, such as a right knee flexion sensor 234, and a means for measuring or determining left knee flexion or extension, such as a left knee flexion sensor 236. In aspects, the right knee flexion sensor 234 may be disposed in a right knee flexion sensor housing 232 and the left knee flexion sensor 236 may be disposed in a left knee flexion sensor housing 230. Each of the left knee flexion sensor housing 230 and the right knee flexion sensor housing 232 may comprise textile-based padding, foam, rubber, plastic, or any other substance capable of protecting the sensor embedded therein. In aspects, one or both of the left knee flexion sensor housing 230 and the right knee flexion sensor housing 232 may also have bracing or compression properties for simultaneous treatment of a pre-existing injury or as a means of protecting against injury.

The right knee flexion sensor 234 and left knee flexion sensor 236 may comprise a piezoresistive sensor, such as a piezoresistor or a flex sensor, or a similar device whose resistance changes with changes in tension or pressure. Said sensors may be analog or digital and may comprise an analog or a digital output. In other aspects, each of the knee flexion sensors may comprise a piezoelectric sensor whose electrical potential changes with changes in tension or pressure. The right knee flexion sensor 234 may be the same or a different type of sensor than the left knee flexion sensor 236. Though pictured on the lateral side of each knee, any one or more knee flexion sensors may be disposed on the medial side, lateral side, or both sides of each knee.

The wearable device 200 may comprise a plurality of sensors designed to measure, among other things, the varus and/or valgus of the knee. In embodiments, such a plurality of sensors comprises a pair of sensors, on each of the left and right legs, configured to measure or monitor the varus and/or valgus of the knees. Seen in FIG. 2A-2B, in such an embodiment, the pair of sensors on the right leg may comprise a right distal varus sensor 228, located distally but proximate to the right knee on an anterior lateral aspect, and a right proximal varus sensor 222, located proximate to the anterior lateral portion of the right hip. The pair of sensors on the left leg may comprise a left distal varus sensor 226, located distally but proximate to the left knee on an anterior lateral aspect, and a left proximal varus sensor 224, located proximate to the anterior lateral portion of the left hip.

Each pair of sensors may be configured to determine knee varus and/or valgus by a variety of means, such as by providing absolute location data, relative positional data, or angular data to the processor 240 using any one or more components or devices discussed in reference to the sensors 116 of system 100. In aspects, if positional or location data is provided to the processor 240, the processor 240 may determine the varus and/or valgus angle, which can be said to be the angular difference between the resting alignment and the in-motion alignment of the sensors. Though exemplary locations of the two pairs of varus sensors are provided, any one or more of the varus sensors may be disposed on any portion of the wearable device 200 such that they are capable of accurately measuring the inward (valgus) or outward (varus) angular deviation of the knee from physiologic norms (neutral). Though discussed in terms of measuring knee varus, the left and right pairs of varus sensors may also be used to determine hip extension during a stork test and hip abduction during a squat test.

In aspects, each of the right knee flexion sensor 234, left knee flexion sensor 236, right proximal varus sensor 222, right distal varus sensor 228, left proximal varus sensor 224, and left distal varus sensor 226 may be connected to the processor 240 via wired or wireless connections. In some aspects, the aforementioned sensors and/or any other sensor on the wearable device may be wired to the processor 240 using conductive thread (not pictured) or conventional insulated electrical wire. In other aspects, the plurality of sensors may wirelessly communicate with the processor 240 using a variety of suitable wireless transmission protocols, including without limitation, Bluetooth, NFC, 802.11, and the like.

The wearable device 200 may further comprise a processor 240. The processor 240 may perform a variety of functions, including receiving analog data such as electrical resistances and/or electric potentials from analog sensors such as a piezoresistors. The processor may also receive digital data from digital sensors such as those discussed in greater detail herein. In aspects the processor 240 may comprise a communication component capable of communicating either raw data or angular data to an external user interface, computer storage, processor, server, or the like, utilizing communication means described with respect to the communication component 120 of system 100 in FIG. 1.

The wearable device 200 may further comprise an event trigger 242. The event trigger 242 exists to cause certain times or movements to be highlighted for follow-up analysis. In aspects, the event trigger 242 is configured in accordance with the event trigger 112 of system 100, described above. As such, the event trigger 242 may comprise a button, switch, toggle, or the like, for manual activation. Additionally or alternatively, the event trigger 242 may comprise an automatic or semi-automatic functionality, wherein the event trigger 242 automatically highlights data when a certain move is detected, such as a slide kick in soccer or a punt in football. In semi-automatic mode, the event trigger 242 may need to be manually activated but the data is only highlighted once a triggering motion is detected, preventing the highlighting of extraneous data.

Turning now to FIG. 2C, a side view of the wearable device 214 is shown. The wearable device 214 is depicted as a brace, wrap, sleeve, or the like, and, when donned, may only cover a portion of the wearer's leg. In all other aspects, the wearable device 214 may be identical to the wearable device 200, including with regard to types and locations of sensors, the configuration of the processor 240 and the event trigger 242. Though only a side view of the right leg of the wearable device 214 is depicted, a corresponding wearable device 214 for the left leg is envisioned.

Figure 3:
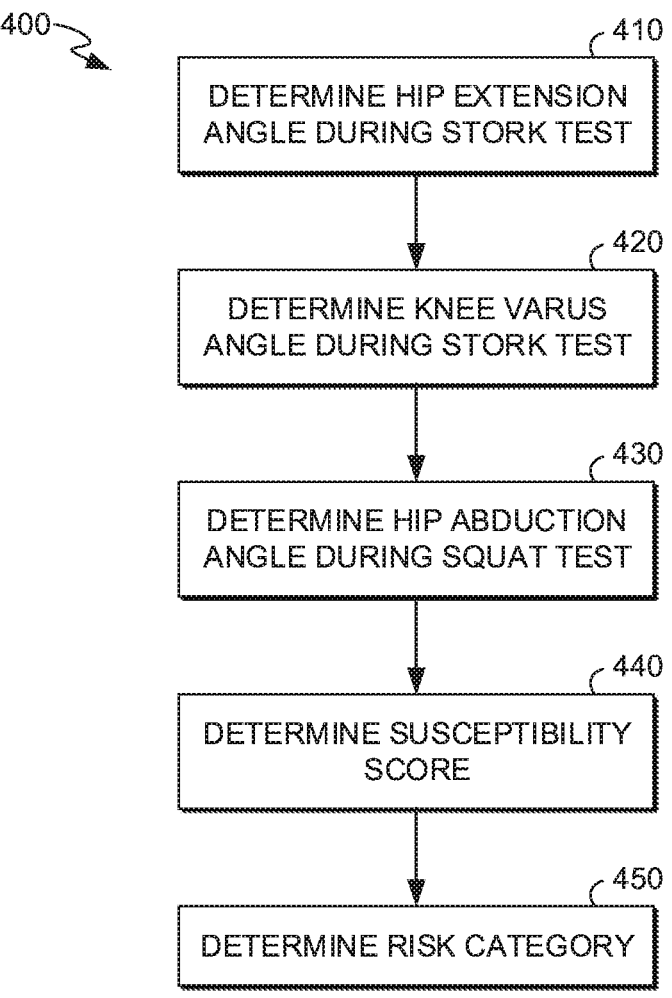
FIG. 3 depicts a flow diagram of an exemplary method for determining susceptibility of injuring an ACL, in accordance with an embodiment of the disclosure.

Turning now to FIG. 3, a method 400 in accordance with the present disclosure is depicted. Method 400 depicts a method for determining ACL injury susceptibility based on angular measurements of certain portions of a human subject's body as the human subject performs various maneuvers. Though depicted in one order, the method 400 specifically may be performed with steps 410, 420, and 430 being performed in any order.

Method 400 comprises step 410, wherein a hip extension angle is determined during a stork test. A stork test, also known as a Gillet test, is conventionally used to indicate mobility impairment of the sacroiliac joint, located at the union of the sacrum and the ilium. Dysfunction of the sacroiliac joint is a common cause of lower back and upper leg pain, thus, the stork test can be used to diagnose the cause of such pain and permit various rehabilitative and pain-mitigating treatments. Conventional use of the stork test calls for physical manipulation of the superficial aspect of the posterior superior iliac spine to determine if, while raising a knee, it moves below (inferior) to its position when at rest. It is not well-known and is unconventional to use the stork test as a basis for determining hip extension or knee varus angles.

At step 410, a human subject will perform the stork test, wherein from a standing position, the human subject will raise one knee as high as comfortable or as high as possible. A right stork hip extension angle can be determined in the anterior-posterior plane when raising the right knee and a left stork hip extension angle can be determined when raising the left knee. The respective stork hip extension angles may be determined by measuring the angle between the resting position of the upper leg and the raised position of the upper leg, using one or more fixed points on the hip as the fulcrum. In some aspects, an angle measured from a posterior reference may be averaged with an angle measured from an anterior reference to obtain the hip extension angle. In aspects, the left stork hip extension angle may be averaged with the right stork hip extension angle to determine a mean stork hip extension angle.

Method 400 comprises step 420, wherein one or more knee varus angles are determined during completion of the stork test. In aspects, the human subject may perform the stork test for a second time in order to complete the knee varus measurements; alternatively, both the hip extension angles and knee varus angles may be measured during the same stork test as in step 410. In aspects, the stork knee varus angle may be measured in the medial-lateral plane on the raised leg during the stork test. In other aspects, the stork knee varus angle may be measured on the planted leg during the stork test. In this manner, a right stork knee varus angle and a left stork knee varus angle may be measured. In aspects, the right stork knee varus angle and the left stork knee varus angle may be averaged to determine a mean stork knee varus angle.

Method 400 comprises step 430, wherein one or more hip abduction angles are determined during completion of a squat. In aspects, the squat test may comprise a human subject performing a squat motion with feet spaced approximately shoulder width apart. In other aspects, the squat test may comprise a human subject performing a squat motion with the left and right heel touching and the toes of each foot pointed outward (similar to a plie). In all aspects, the angle in the medial-lateral plane created by the abduction of the hips may be measured to obtain a left squat hip abduction angle and a right squat hip abduction angle. In aspects, the right squat hip abduction angle and the left squat hip abduction angle may be averaged to determine a mean squat hip abduction angle.

Determination or measurement of the angular values in steps 410, 420, and 430 may be achieved in any or more of a variety of ways. In aspects, manual angular measuring tools such as a speed square or a protractor may be used. In other aspects, visual detection tools and methods such as markerless motion capture, 3D camera capture, marker-based optical motion capture, etc., may be used. In yet other aspects, a wearable device, such as the wearable device 200 or the wearable device 214 may be utilized.

Method 400 further comprises determining a susceptibility score in step 440. The susceptibility score (represented by the outcome "S" in the equation below) comprises the mean stork hip extension angle (represented by variable "A" in the equation below), the mean stork knee varus angle (represented by variable "B" in the equation below), and the mean squat hip abduction angle (represented by variable "C" in the equation below), weighting values that determine the impact of the variable on the overall score, and a constant (represented by variable "K" in the equation below. Though not included in the equation below, the susceptibility score may also include a second constant that may represent the existence and/or severity of a prior ACL injury. An example of an equation that may be used to determine the susceptibility score follows:

$$S = \frac{e^{(K+.69A-1.68B+.85C)}}{\left(1 + e^{(K+.69A-1.68B+.85C)}\right)}$$

The susceptibility score "S" may be a positive decimal figure, and may be used to determine the risk category in step 450. Assigning a risk category to the susceptibility score simplifies the manner in which the information can be interpreted by athletes, training staff, or any other user. In aspects, risk categorization comprises assigning a risk category to a susceptibility score based on the score exceeding a threshold of three equal tiers equating to low risk, moderate risk, and high risk. For example, a susceptibility score of 0.4 may exceed the threshold of medium risk, which may be set at 0.33, but may not exceed the threshold of high risk, which may be set at 0.66. Accordingly, such a susceptibility score would be assigned a category of moderate risk. It is envisioned that various treatment and precautionary protocols may be implemented based on the risk category. For example, in the low risk category, athletes may be encouraged to periodically monitor or repeat the method 400. In the moderate risk category, physical therapy may be used to correct or mitigate certain locomotive attributes of the athlete. In the high risk category, corrective devices may be used in combination with physical therapy to limit certain bodily movements, such as twisting of the knee, knee hyperextension, etc.

Figure 4:
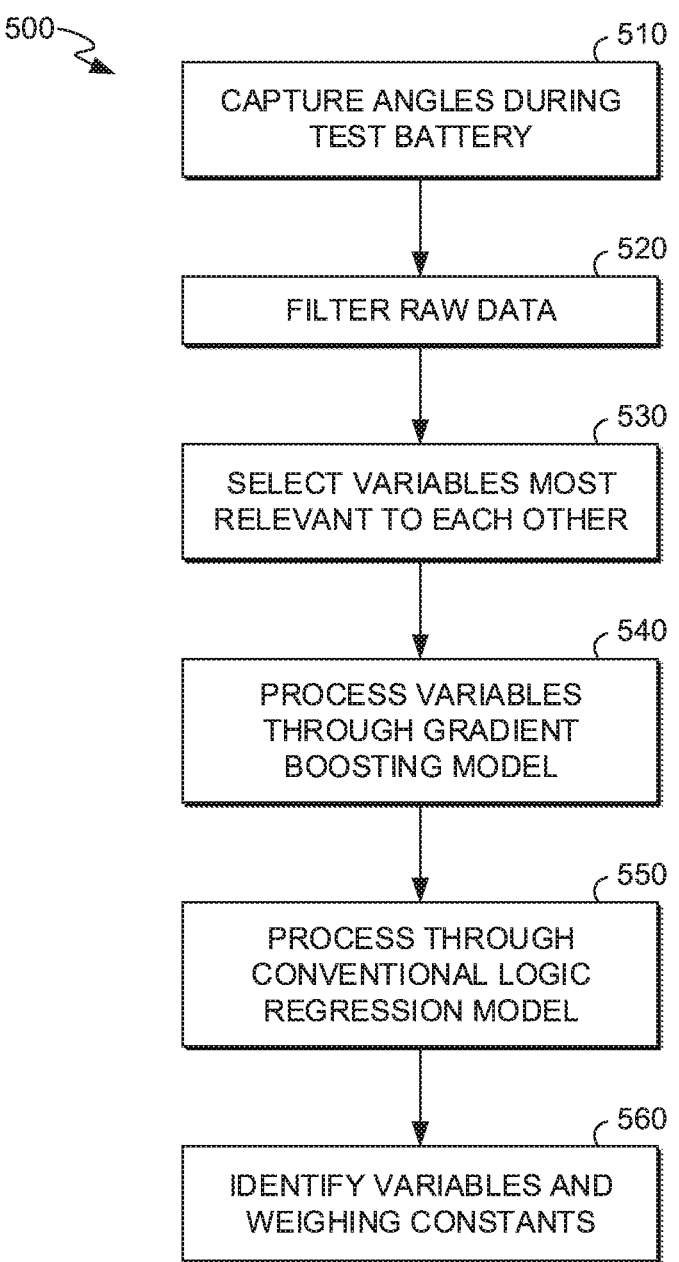
FIG. 4 depicts a flow diagram of an exemplary method for identifying variables for use in an injury susceptibility determination, in accordance with an embodiment of the disclosure.

Turning now to FIG. 4, a mechanics-based method 500 for identifying variables and weighting constants is depicted in accordance with the present disclosure. The method 500 may be used to identify quantitatively measurable variables that may accurately indicate susceptibility of a human subject to sustain an injury to a particular part of the body. In aspects, the method 500 may be utilized for identifying variables for injury to a portion of the extremities. An example of the utilization of method 500 is identifying variables and weighting constants such as those used in method 400 to quantitatively determine physiologic susceptibility of an ACL injury. In other aspects, the method 500 may be used for identifying susceptibility for injuries of non-extremities. As an example, method 500 may be utilized to identify variables that may quantitatively indicate susceptibility of a human subject to sustain future injuries to portions of the body, such as the Medial Collateral Ligament (MCL), meniscus, iliotibial band, or to suffer from conditions such as shin splints or plantar fasciitis. Not shown in FIG. 4, the method 500 optionally may comprise a health questionnaire, wherein medical histories, including previous relevant injuries, age, height, weight, etc., may be obtained.

Method 500 comprises step 510, wherein motion-based data is captured. In step 510, a human subject may be subjected to a battery of relevant mechanics-based tests. For example, a method used to identify variables and weighing constants for susceptibility of shin splints may comprise foot and leg movements that permit the capture of angular data in relevant planes for flexion, dorsiflexion, extension, abduction, adduction, and the like. Angular data captured in step 510 may utilize systems, devices, and methods, conceptually similar to those disclosed herein with regard to system 100, device 200, or method 400.

Method 500 further comprises step 520, wherein a coarse filter is applied to captured data. The coarse filter step 520 reduces the scope of the captured data in order to reduce processing time and resources necessary to process the remaining data into a usable set of variables. In aspects, any variable missing over 10% of measured data (for example as a result of measurement or movement difficulty) may be eliminated. In other aspects, any variable having a standard deviation of zero may be eliminated. In some aspects, non-measurement data, such as existence of prior injuries may be eliminated. The resulting coarse filtered data is input to step 530.

Method 500 also comprises step 530, wherein one or more regression analyses are completed on the coarse filtered data in order to select variables most relevant to each other. In aspects, the regression analysis may comprise using a Least Absolute Shrinkage and Selection Operator (LASSO), wherein variables are selected and normalized based on their statistical relationships to one another. In other aspects, any regression tool or method may be used to achieve the same desired effect of selecting variables most relevant to each other, such as using Tikhonov regularization, matrix regularization, and the like. The regression analysis produces a regularization path over a grid of values for the tuning parameter of $\lambda=10$, creating regularized variable values, many of which may become statistical nulls.

Method 500 comprises step 540, wherein the regularized variable values are processed through one or more boosting models. In aspects, the boosting model may comprise a gradient boosting model. In other aspects, any regression and/or generalization model may be utilized to produce grouped prediction models comprising multiple variables. In some aspects, only values exceeding a threshold, such as $1\times10^{-4}$ may be passed into the boosting model.

Method 500 further comprises step 550, wherein the grouped prediction models comprising multiple variables are processed through a second regression model. In aspects, the second regression model may comprise a conventional logistic regression model. In other aspects, the second regression model may comprise any linear or multilevel regression model in which one or more grouped prediction models comprising multiple variables are determined to be most predictive of susceptibility of injury. In step 560, the plurality of variables and their associated weighing constants are identified and compiled to be used in an assessment method similar to method 400. A general susceptibility score, S, may be calculated where $A_n$ represents the weighing constant associated with the Nth variable, whose measured value is represented by $V_n$:

$$S = \frac{e^{\left(K+\Sigma_1^N A_n V_n\right)}}{\left(1 + e^{\left(K+\Sigma_1^N A_n V_n\right)}\right)}$$

Many different arrangements of the various components and steps depicted, as well as components and steps not shown, are possible without departing from the scope of the present disclosure and claims below. Embodiments have been described herein with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. A lower-body garment for identifying a human subject's physiologic susceptibility of ACL injury, comprising:
   a torso portion having a waist opening;
   a first leg portion and a second leg portion extending from the torso portion, the first leg portion defining a first leg opening and the second leg portion defining a second leg opening;
   one or more sensors coupled to the torso portion, the first leg portion and the second leg portion at locations proximate the human subject's hip and/or knees, configured to:
      measure a first value characterizing knee varus while a wearer of the lower-body garment is subjected to a stork test; and measure a second value characterizing hip extension while the wearer of the lower-body garment is subjected to the stork test; and
      communicate the first value and the second value to one or more computer processing components;
   one or more computer processing components coupled to the lower-body garment;
   a non-transitory computer-readable medium coupled to the one or more computer processing components, the non-transitory computer-readable medium comprising computer-executable instructions stored thereon that, when executed by the one or more computer processing components, cause the one or more computer processing components to:
      receive the first value and the second value from the one or more sensors;
      calculate a susceptibility score using a predetermined algorithm that processes the first value and the second value to determine a mean hip extension angle, a mean knee varus angle, and a mean hip abduction angle; and
      output the susceptibility score.

2. The lower-body garment of claim 1, wherein the one or more sensors are further configured to measure a third value characterizing hip abduction while the wearer of the lower-body garment is subjected to a squat test and communicate the third value to the one or more computer processing components.

3. The lower-body garment of claim 1, wherein the one or more processors are coupled to the lower-body garment.

4. The lower-body garment of claim 3, wherein each of the one or more sensors are communicatively coupled to the one or more processors via a wireless connection.

5. The lower-body garment of claim 3, wherein the lower-body garment comprises a first textile layer and a second textile layer, and wherein the one or more sensors are disposed between the first textile layer and the second textile layer.

6. The lower-body garment of claim 1, wherein the one or more sensors comprise a first sensor coupled to the lower-body garment proximate to the torso portion and a second sensor coupled to the first leg portion of the lower-body garment in a location that is distal and proximate to a knee region when the lower-body garment is in an as-worn configuration.

7. The lower-body garment of claim 1, further comprising an event trigger, wherein activation of the event trigger causes the one or more sensors to measure at least one of the first value and the second value.

8. The lower-body garment of claim 1, further comprising a knee flexion sensor coupled to the lower-body garment proximate to a knee region when the lower-body garment is in an as-worn configuration, wherein the knee flexion sensor is configured to measure knee flexion and communicate a fourth value characterizing knee flexion to the one or more computer processing components, and wherein the susceptibility score is based at least in part on the first value, the second value, and the third value.

9. A device for monitoring susceptibility of injury to a lower extremity comprising:
   a housing for retaining one or more sensors proximate to a wearer's hip and/or knees when in an as-worn configuration;
   one or more sensors to measure a first value characterizing hip extension and a second value characterizing knee varus while a wearer of the device is subjected to a stork test; and one or more computer processing components, wherein the one or more computer processing components comprise a machine-readable medium including executable instructions stored thereon which, when executed by the one or more computer processing components, implement a method for determining the susceptibility of lower extremity injury comprising:

determining a mean hip extension angle;

determining a mean knee varus angle;

determining a mean hip abduction angle;

generate a susceptibility score based at least in part on the first value, the second value, the mean hip extension angle, the mean knee varus angle, and the mean hip abduction angle; and causing a display on a user interface, the susceptibility score.

10. The device of claim 9, wherein the lower extremity comprises an ACL.

11. The device of claim 9, further comprising an event trigger, wherein activation of the event trigger causes the processor to obtain measurement data for a preset time period.

12. The device of claim 9, wherein the one or more sensors comprises a first sensor disposed proximate to a knee of the wearer's body and a second sensor disposed proximal to the first sensor, on the same leg of the wearer, when the device is in an as-worn configuration.

13. The device of claim 9, wherein the housing comprises a garment.

14. The device of claim 9, wherein the one or more sensors are communicatively coupled to the one or more computer processing components via a wireless connection.

15. The device of claim 9, wherein the one or more sensors are connected to the one or more computer processing components via conductive thread.

16. The device of claim 9, wherein the one or more sensors further comprise a knee flexion sensor.

17. The device of claim 16, wherein the knee flexion sensor comprises a piezoresistor.

18. The device of claim 16, wherein the knee flexion sensor comprises a flex resistor.

\* \* \* \* \*